United States Patent
Van Tassel et al.

[11] Patent Number: 5,855,559
[45] Date of Patent: Jan. 5, 1999

[54] HEMOSTATIC AGENT DELIVERY DEVICE HAVING BUILT-IN PRESSURE SENSOR

[75] Inventors: Robert A. Van Tassel, Excelsior; Robert S. Schwartz; David Holms, both of Rochester; Mark A. Rydell, Golden Valley, all of Minn.

[73] Assignee: Tricardia, Inc., Excelsior, Minn.

[21] Appl. No.: 800,047

[22] Filed: Feb. 14, 1997

[51] Int. Cl.⁶ .................................................. A61B 5/00
[52] U.S. Cl. ........................................... 600/486; 600/505
[58] Field of Search .............................. 600/486, 487, 600/500, 504, 505

[56] References Cited

U.S. PATENT DOCUMENTS

| | | | |
|---|---|---|---|
| 3,911,902 | 10/1975 | Delpy | 128/2.05 |
| 3,942,382 | 3/1976 | Hök | 73/398 |
| 4,190,057 | 2/1980 | Hill et al. | 122/675 |
| 4,531,943 | 7/1985 | Van Tassel et al. | 604/280 |
| 4,738,658 | 4/1988 | Margo et al. | 604/53 |
| 4,744,364 | 5/1988 | Kensey | 128/334 |
| 4,779,625 | 10/1988 | Cole | 128/673 |
| 4,809,709 | 3/1989 | Brooks | 128/748 |
| 4,838,280 | 6/1989 | Haaga | 128/751 |
| 4,852,568 | 8/1989 | Kensey | 128/325 |
| 4,852,974 | 8/1989 | Melzig et al. | 350/165 |
| 4,878,898 | 11/1989 | Griffin et al. | 604/101 |
| 4,890,612 | 1/1990 | Kensey | 606/213 |
| 4,901,731 | 2/1990 | Millar | 128/675 |
| 4,924,872 | 5/1990 | Frank | 128/673 |
| 4,928,693 | 5/1990 | Goodin et al. | 128/637 |
| 5,021,059 | 6/1991 | Kensey et al. | 606/213 |
| 5,041,129 | 8/1991 | Hayhurst et al. | 606/232 |
| 5,129,882 | 7/1992 | Weldon et al. | 604/96 |
| 5,192,300 | 3/1993 | Fowler | 606/213 |
| 5,221,259 | 6/1993 | Weldon et al. | 604/96 |
| 5,222,974 | 6/1993 | Kensey et al. | 606/213 |
| 5,281,197 | 1/1994 | Arias et al. | 604/57 |
| 5,290,310 | 3/1994 | Makower et al. | 606/213 |
| 5,324,306 | 6/1994 | Makower et al. | 606/213 |
| 5,447,502 | 9/1995 | Haaga | 604/265 |
| 5,454,374 | 10/1995 | Omachi | 128/673 |

FOREIGN PATENT DOCUMENTS

0476178A1  2/1990  European Pat. Off. .

Primary Examiner—Marvin M. Lateef
Assistant Examiner—Eleni Mantis Mercader
Attorney, Agent, or Firm—Haugen and Nikolai, P.A.

[57] ABSTRACT

An instrument for achieving rapid hemostasis at the conclusion of a catheterization procedure comprising a hemostatic agent injection device for use with a conventional introducer sheath used to gain access to the blood vessel. The injection device includes an elongated tubular member having ejection ports proximate its distal end. A hub member is located on the proximal end of the tubular member and includes an elongated groove or track located in its surface with a transparent cover. The enclosed track is in fluid communication with the lumen extending through the tubular member. After the catheterization procedure, the instrument is inserted into the introducer sheath. Blood flows into the lumen of the device and into the enclosed track. The leading edge of the blood pulsates within the enclosed track, clearly indicating that the ports are located in the blood vessel and subjected to variations in blood pressure. The instrument and introducer sheath are then slowly retracted as a unit in the puncture wound. The blood flow will stop pulsating in the enclosed track when the ports have exited the blood vessel wall. A hemostatic agent is then injected by the instrument adjacent the vessel wall.

29 Claims, 7 Drawing Sheets

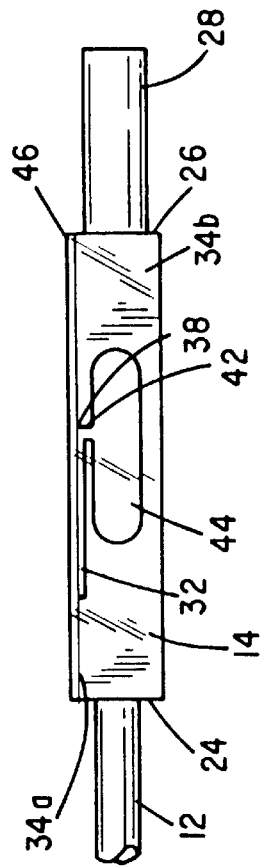
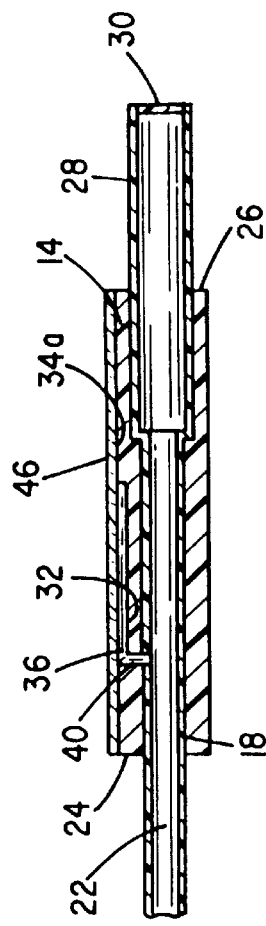
FIG. 2
FIG. 3
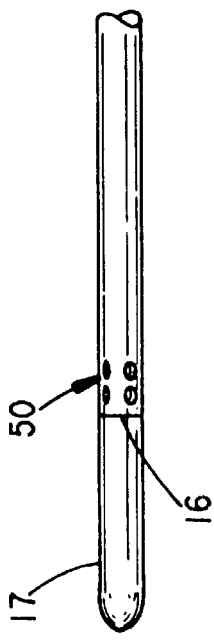
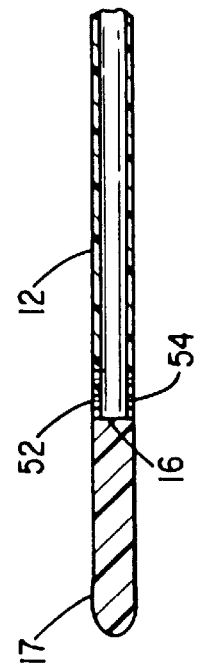

HEMOSTATIC AGENT DELIVERY DEVICE HAVING BUILT-IN PRESSURE SENSOR

I. Field of the Invention

This invention relates generally to a surgical device which is used in catheterization procedures, and more particularly, to a device with a pressure sensing feature used to inject a hemostatic agent at the end of the catheterization procedure.

II. Discussion of the Prior Art

In a percutaneous intravascular procedure, such as performing an angioplasty or angiography, access to the vascular space is generally obtained by using the so called Seldinger technique. In this technique, a hollow needle is used to create a puncture wound through the skin, the underlaying muscle tissue and through the wall of selected blood vessel, such as the femoral artery. Next, a guide wire is inserted through the tubular needle until its distal end is located in the blood vessel. The needle is then removed from the guide wire and replaced with an introducer sheath and dilator. The introducer sheath typically will include a self-sealing hemostatic valve on its proximal end. The guide wire is then advanced into the vascular space through the introducer and directed to a preselected area of the vascular system. Once the guide wire is positioned, a catheter, such as a balloon catheter in the case of a balloon angioplasty procedure, is advanced over the guide wire until the balloon is at a selected location, such as a stenosis in a coronary artery.

At the conclusion of the procedure, when the catheter, guide wire and introducer sheath are removed from the puncture site there may be profuse bleeding, hematoma or dissections, especially where the patient has been on an anticoagulant therapy, such as heparin, coumadin, aspirin or alpha, $beta_{II}$ blockade thrombolytic agent. Manual pressure may have to be applied for a prolonged time period to obtain hemostasis. So as to not unduly tie-up trained medical personnel, an external vascular clamp, sand bags or a pressure dressing may be used to apply pressure to the puncture site to help ensure satisfactory, permanent hemostasis.

Prior art methods have addressed the problem of achieving hemostasis following removal of a percutaneously applied intravascular introducer in such uses as angiography or angioplasty. The Makower et al. U.S. Pat. No. 5,290,310 describes a device for delivering a hemostatic substance subcutaneously against a penetration site in the wall of a blood vessel. An instrument containing a toroidal-shaped collagen plug within a barrel thereof is made to surround the exterior of the tubular introducer. The instrument includes a pusher mechanism for injecting the collagen plug into the puncture wound and against the exterior wall of the blood vessel at the site of the puncture.

The Weldon et al. U.S. Pat. No. 5,129,882 also discloses a surgical implement for injecting a hemostatic agent in a puncture wound by routing the injection device through the lumen of the introducer sheath after it has been retracted sufficiently so that the distal end thereof is no longer in the blood vessel. Then, by deploying a plunger, the hemostatic agent is forced out of the instrument and against the exterior wall of the artery proximate the puncture wound.

Pat. Nos. 4,744,364, 4,852,974, 4,890,612, 5,021,059 and 5,222,974, issued to Kenneth Kensey, each describe a method and apparatus for effecting hemostasis by first inserting an anchoring device through the puncture wound and into the blood vessel while using a filament attached to the anchoring device to hold it in place as an appropriate sealant is injected into the wound. The anchoring device prevents entrance of the sealing material into the blood vessel and serves as anchor and guide for addressing selected vessels.

Other devices for injecting a hemostatic agent into a puncture wound following a vascular procedure include the Arias et al. U.S. Pat. No. 5,281,197, the Haaga U.S. Pat. No. 4,838,280, the Fowler U.S. Pat. No. 5,192,300, the Magro et al. U.S. Pat. No. 4,738,658 and published European Patent Application 0 476 178 A1 of Bioplex Medical, B.V. Furthermore, pending application Ser. No. 08/629,022, of which some of the present inventors are named as co-inventors, addresses the problem by providing a self-contained assembly of a combined introducer sheath, introducer dilator and a device for effecting hemostasis following a vascular procedure.

For the most part, these references describe devices that are intended to be used in combination with the tubular introducer sheath for deploying a hemostatic agent following withdrawal of any guide wire, guide catheter or working catheter at the conclusion of the procedure. These devices require significant skill in their use to preclude potential complications occasioned by unwanted placement of the hemostatic agent within the blood vessel itself.

A need exists for a device for effecting hemostasis following a vascular procedure which can be inserted into the introducer sheath and which will indicate whether its ejection port is within the blood vessel. In our earlier design described in the aforereferenced application, we depended on a flash of blood flowing into a transparent tube to indicate that the ejection ports on the combined introducer and hemostatic injection device were exterior to the blood vessel. When the device of the present invention indicates that the ejection ports are outside the blood vessel, the hemostatic agent can then be injected into a lumen of the device leading to the ejection ports on the device at a location proximate the outer wall of the blood vessel to be sealed. Such a device effectively insures that the hemostatic agent will not be injected into the blood vessel.

While the prior art has included catheters with pressure sensing devices, such as the Brooks Pat. No. 4,809,709, Griffin et al. Pat. No. 4,878,898, Miller Pat. No. 4,901,731, Frank Pat. No. 4,924,872 and the Goodin et al. Pat. No. 4,928,693, no provision has been made in these devices for injecting a hemostatic fluid nor do they describe a pressure indicator that comprises a pulsation type micro-manometer.

SUMMARY OF THE INVENTION

The present invention is a device for sealing percutaneous punctures in a blood vessel that is used in conjunction with a tubular introducer sheath having a distal end insertable into a wound resulting from a percutaneous puncture in a blood vessel wall. The device consists of an elongated tubular member having a hub member on its proximal end and a soft tip and ports proximate its distal end. The elongated tubular member has a lumen extending therethrough. The lumen is closed at its distal end and its proximal end terminates at a hemostatic seal in the hub.

The hub member also includes an elongated grooved track formed on its outer surface. A transparent member overlays the grooved track and cooperates with the groove to form a sealed fluid tight track. A transverse bore extends from a first end of the grooved track to the lumen of the tubular member. A second transverse bore extends from the second end of the grooved track to a fluid tight air compression chamber. This chamber may be formed on the exterior surface of the hub member or it may be formed in the hub member between the outer surface and the lumen of the tubular member. If the chamber is formed on the outer surface, the transparent member overlays this also to form a sealed fluid tight chamber.

The tubular member is sized so that it fits within the lumen of the introducer sheath with the soft distal tip and ports extending out of the distal end of the sheath into the blood vessel. The plurality of ports are in fluid communication with the lumen extending through the tubular member.

The device is used following the conclusion of the catheterization procedure. The catheter and guide wire are removed leaving the tubular introducer sheath with its proximal end extending outside the puncture and the distal end extending through the puncture in the vessel wall with its distal end open into the vessel. The distal end of the tubular member is inserted into the sheath with the hub of the sealing device remaining proximate the proximal end of the tubular introducer sheath.

As the distal end of the sealing device exits the introducer and enters the vessel, blood will enter the ejection ports, flow up the lumen of the sealing device and into the first transverse bore leading to the sealed grooved track. The flow of blood stops once the air trapped ahead of the blood flow in the sealed grooved track and compression chamber reaches equilibrium with the blood pressure. As blood pressure changes from systolic pressure to diastolic pressure, blood pulsates back and forth in the track. Because of the transparent overlay, the pulsating blood is highly visible, thus operating as a micro-manometer.

The sheath and the sealing device are then slowly retracted as a unit. The visible oscillating movement of blood in the grooved track stops as soon as the ejection ports leave the blood vessel. At that time, a hemostatic agent is injected via a syringe into the lumen of the tubular member through a valve on the hub. The hemostatic agent then exits the ports to deposit a predetermined quantity thereof into the puncture wound, but not into the blood vessel. The sealing agent remains in place following removal of the introducer sheath and the sealing device from the puncture wound.

In a first alternative embodiment, the tubular member includes a thin compliant membrane comprising the wall between the ports and the soft distal tip. A positioning wire extends through the lumen of the tubular member and is anchored at its distal end to the soft distal tip. The wire's proximal tip extends out of the tubular member for manipulation by the physician. The wire is used to move the thin membrane into two positions. In the first position the thin membrane wall is substantially in line with the exterior wall of the tubular member. In the second position, the wire is pulled in the proximal direction to move the distal tip towards the ports. This movement causes the thin membrane wall to flex and fold so that is forms an annular disc surrounding the tubular member between the ports and the distal tip. During the procedure, the thin membrane is initially in its first position. As the ports are positioned outside of the patient's blood vessel, the wire is pulled to position the annular disc formed by the thin membrane adjacent the puncture site forming a temporary plug. The hemostatic agent is then injected into the puncture site and prevented from entering the blood vessel due to the temporary plug. After the hemostatic agent is injected, the wire is pushed in the distal direction returning the thin membrane to its first position and the tubular member is removed before the hemostatic agent solidifies at the puncture site.

In a second alternative embodiment, a dual syringe assembly is used to inject a hemostatic agent consisting of platelet rich product and thrombin product mixture into the indicator. The syringe assembly includes two hypodermic syringes coupled to a manifold. The syringes are coupled by a molded plastic cap at the upper end of the syringe assembly so that when the cap is depressed both syringes are simultaneously deployed. The larger syringe contains a platelet rich product or fibrin-rich product obtained from the patient and the smaller diameter syringe contains thrombin or other activator. When the two mix, they create a semi-solid plug like material in about two minutes after they are mixed. This is sufficient time for the mixture to travel through the indicator device and out the ejection port before solidifying in the puncture area.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which:

FIG. 2 is a side elevational view of the present invention;

FIG. 3 is a cross-sectional view taken along line 3—3 in FIG. 1;

DETAILED DESCRIPTION OF THE PREFERRED EMBODIMENT

Figure 1:
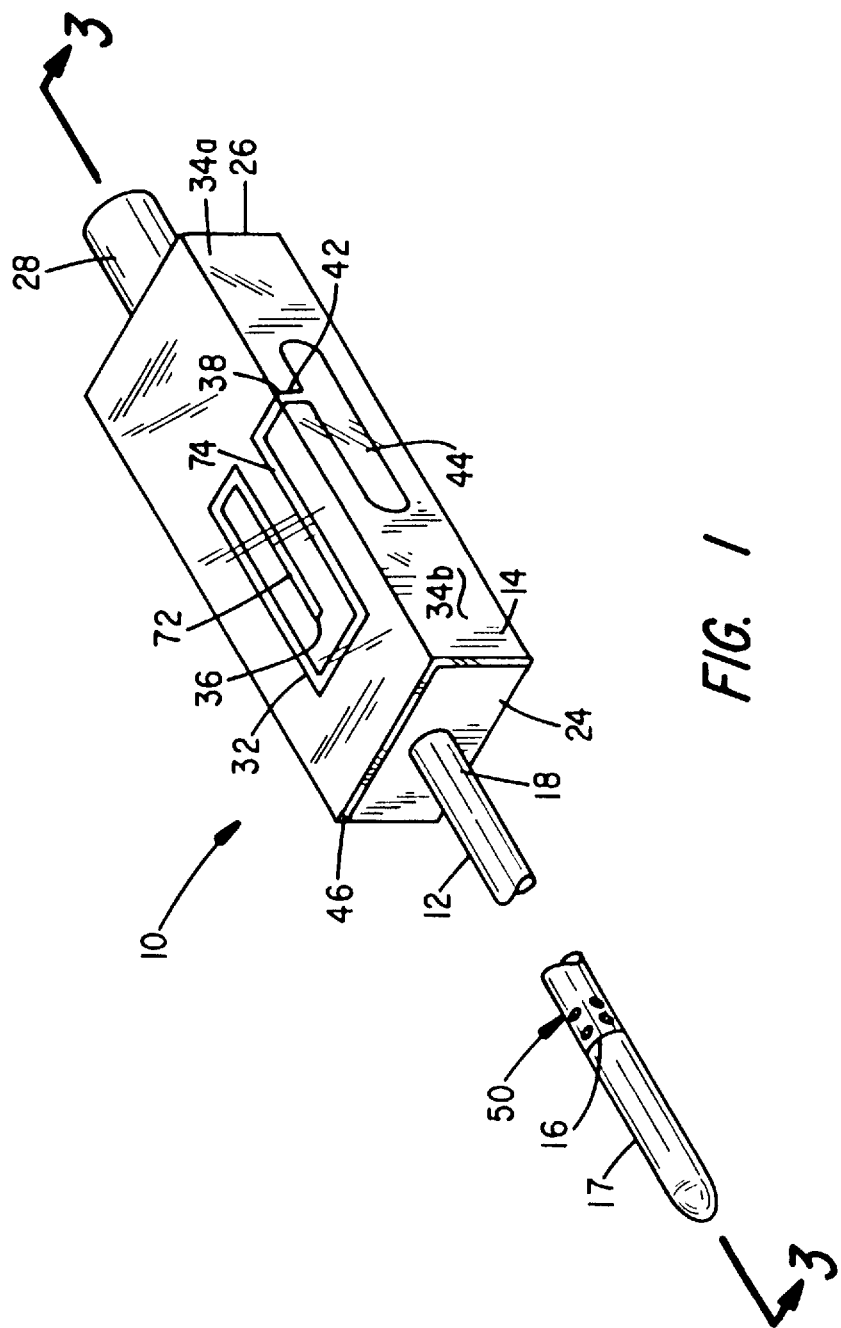
FIG. 1 is a perspective view of the present invention.

A device for sealing percutaneous punctures in the blood vessel and having a built-in pressure indicator is shown in FIG. 1 and is indicated generally by numeral 10. It is comprised of an elongated tubular member 12 with a hub member 14 on its proximal end. The tubular member 12 has a distal end 16 and a proximal end 18 which extends into a distal end 24 of the hub member 14. Attached to the distal end 16 of tubular member 12 is an elongated, highly flexible soft plastic extension 17 that seals the distal end 16 of the tubular member 12. A lumen 22 (FIG. 3) extends the length of the tubular member 12. Affixed to the proximal end of the lumen 22 and extending partially into a proximal end 26 of the hub member 14 is an integrally molded or an otherwise affixed hemostatic seal housing 28. The seal 30 typically comprises one or more elastomeric discs having self closing slits formed through the thickness to cooperate with any instrument that may be inserted into the slits, such as the end of a hypodermic syringe to block the flow of blood out through the proximal end of the lumen 22.

The hub 14 includes an elongated grooved track 32 formed into its exterior surface of its upper surface 34a as seen in FIGS. 1–3. The grooved track 32 has a first end 36 and a second end 38 and may be convoluted as shown or any other suitable configuration. The first end 36 of the grooved track 32 opens into a first transverse bore 40 (FIG. 3) that provides the fluid communication between the lumen 22 and the grooved track 32. The second end 38 of the grooved track leads to an enlarged chamber 44. As shown in FIGS. 1 and 2, the chamber is shown as being formed into the exterior surface of side wall 34b of the hub 14. However, the chamber 44 can be formed into the top surface 34a or even internally formed and positioned between the exterior surface of the hub 14 and the lumen 22. A transparent cover member 46 overlays the grooved track 32 and the chamber 44 to form a fluid tight seal. The enclosed sealed grooved track 32 may be coated with heparin to reduce any tendency for blood entering the track 32 to coagulate.

The soft deformable tip 17, positioned on the distal end 16 of the tubular member 12, may comprise an elastomeric material having a durometer less than about 70 shore A. Immediately proximal of the soft tip 17 are a plurality of ejection ports, designated generally as 50. These ejection ports 50 provide a fluid passageway from lumen 22 to the exterior of tubular member as shown by ports 52 and 54 in FIG. 3. The tubular member 12 has a sufficient length such that the soft tip 17 and the ports 50 will extend out of the distal end of the vascular introducer with which it is used when the tubular member 12 is inserted into the vascular introducer, as will be further explained when the operation of the device is discussed with the aid of FIGS. 4 through 6.

Figure 5:
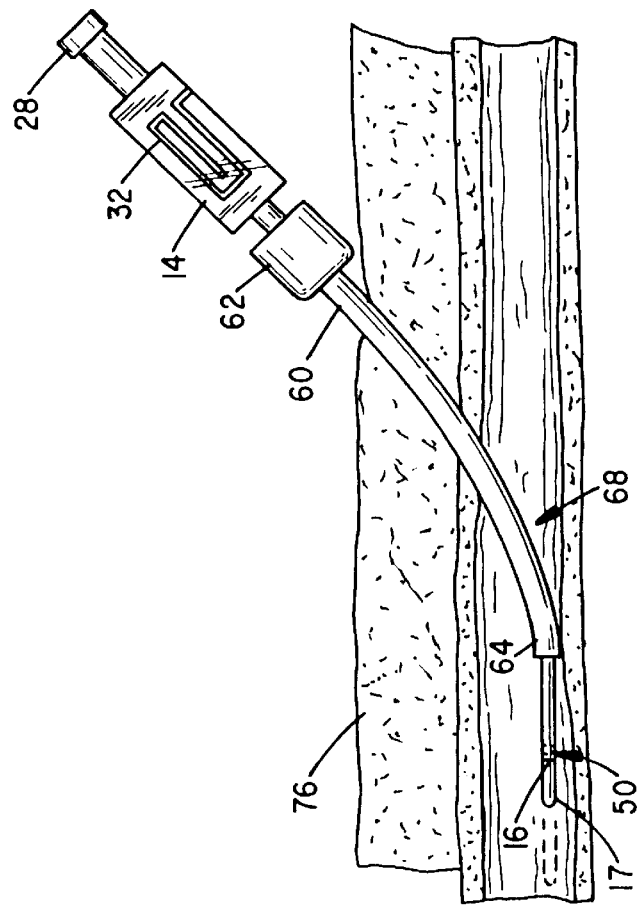
FIG. 5 is a side elevational view of the present invention fully inserted into the introducer sheath of FIG. 4.
Figure 4:
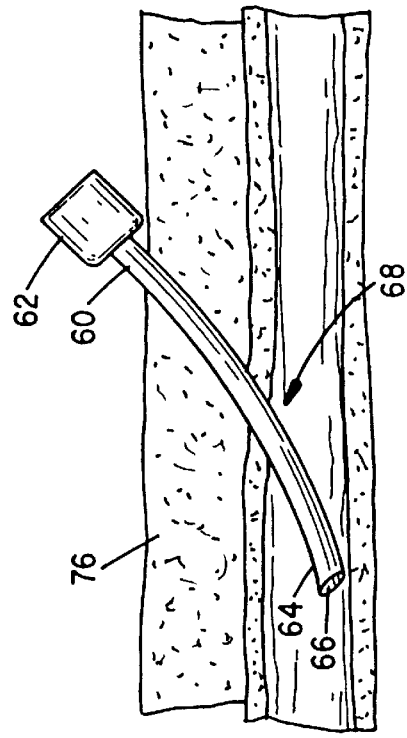
FIG. 4 is a side elevational view of introducer sheath used with the present invention as it remains in the patient near the completion of a catheterization procedure.
Figure 6:
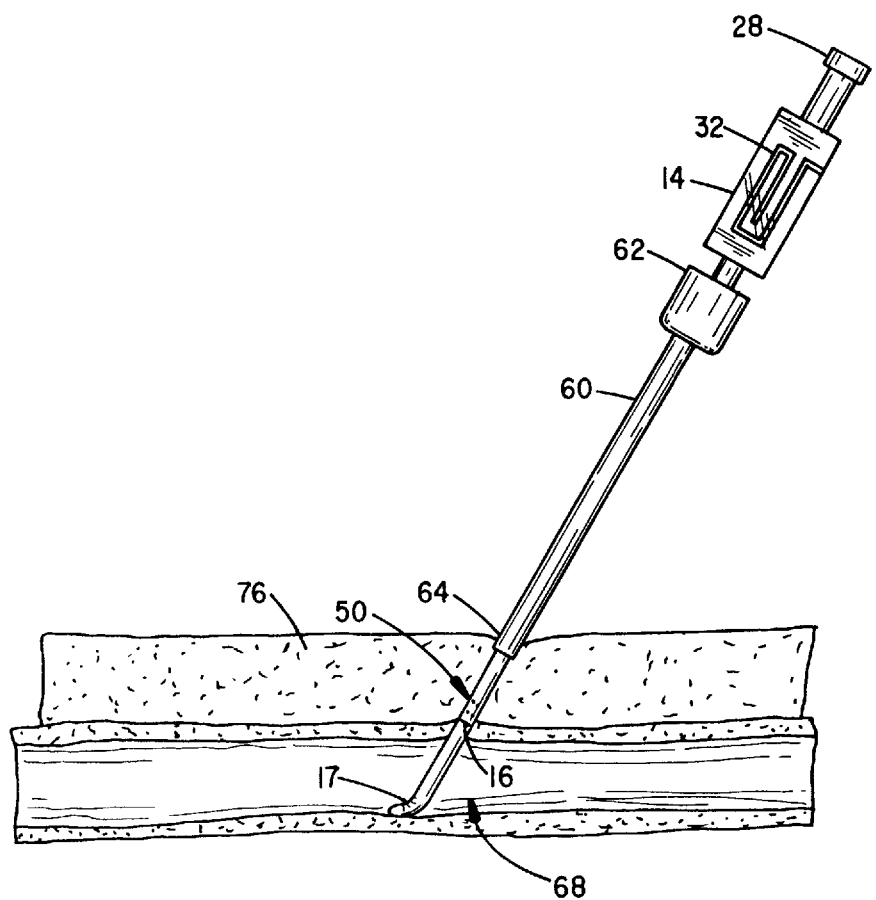
FIG. 6 is a side elevational view of the present invention and introducer sheath partially removed from the patient.

In use, toward the termination of the catheterization procedure, any working catheters, guide catheters and guide wires will be stripped out of the proximal end of the introducer sheath, designated 60 in FIGS. 4, 5 and 6, with the introducer sheath 60 remaining in place as seen in FIG. 4. The introducer sheath 60 has proximal hub 62 and a distal end 64 and a lumen 66 extending therebetween. The physician will slide the tubular member 12 of the hemostatic agent injection device 10 down the lumen 66 of the introducer 60 until the soft tip 17 and ports 50 extend out of the distal end of the introducer sheath 60 into the blood vessel 68. The hub 14 is larger than the hub 62 of the sheath 66 and hence, the hub 62 serves as a stop, limiting the extent that the soft end 17 of the device 10 can enter the blood vessel 68.

As the ports 50 enter the sheath 60 and blood vessel 68, blood travels into the lumen 22 of the device 10, through the first transverse bore 40 and into the sealed grooved track 32. As the blood enters, air ahead of the blood flow is trapped in the sealed grooved track 32 and chamber 44. Chamber 44 operates as an air compression chamber by having a predetermined volume that enables the blood pressure to compress the air trapped ahead of the blood flow in the sealed grooved track 32 and chamber 44 resulting in blood flow into the sealed grooved track 32. When the pressure of the trapped air reaches equilibrium with the blood pressure, blood stops filling the sealed track 32. As the blood pressure varies between systolic and diastolic pressure levels, the blood will appear to oscillate back and forth in the track. The blood movement is highly visible because of the transparent cover member 46. As shown in FIG. 1, number 72 designates a location of the leading edge of the blood flow when at diastolic pressure and number 74 designates the leading edge of blood at systolic pressure.

The device 10 and introducer sheath 60 are then slowly retracted as a unit while the physician views the oscillating movement of the blood in the track. When the movement of the blood stops, this indicates that the ejection ports 50 are now in the tissue 76 and out of the blood vessel 68 as shown in FIG. 6. The hemostatic agent may now be injected through hemostatic seal member 30 on the hub 14 of the device 10. The hemostatic agent is made to flow through the lumen 22 where it ultimately exudes out of the ejection ports 50 of the tubular member 14. Normal blood pressure can be relied upon to prevent the hemostatic agent from entering the blood vessel 68 upon removal of the sheath 60 and device 10.

The fluid hemostatic agent employed in carrying out the present invention may be a clotting agent, such as thrombin, fibrin, fibrin glue, platelet glue or a collagen slurry or gel. It may also comprise a tissue adhesive, such as methacrylates or cyanocrylates. Vasoconstrictive drugs, such as phenylephrine, norepinephrine, epinephrine, prostaglandin F2 alpha endothelin, methergine, oxytocin and isoprel may also be used in stemming blood flow. Other astringent substances, such as ferric chloride, zinc oxide, permaganates or tannic acid can be approximately formulated with colors, binders or matrix materials so as to have a sufficiently low viscosity to permit introduction, through the lumen 22.

Figure 7:
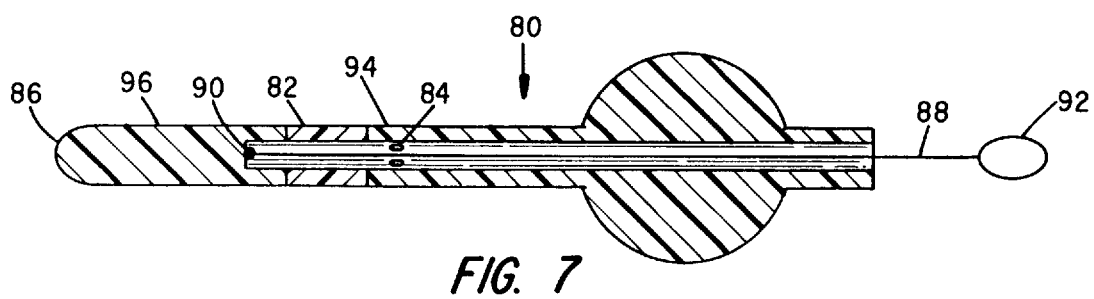
FIG. 7 is a cross sectional view of a first alternative embodiment of the tubular member in its first relaxed position.
Figure 8:
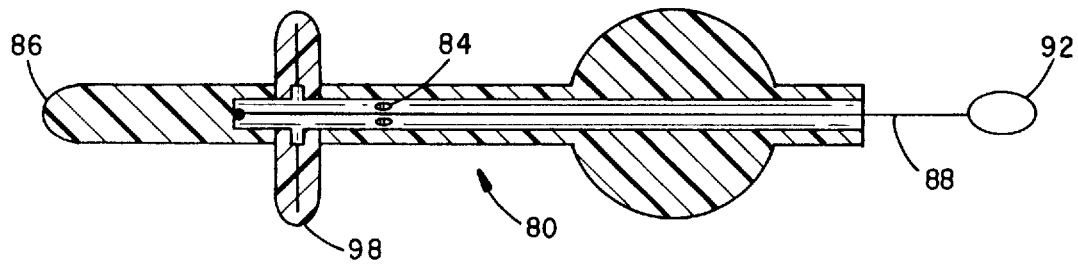
FIG. 8 is a cross sectional view of the first alternative embodiment of the tubular member in its second contracted position.
Figure 9:
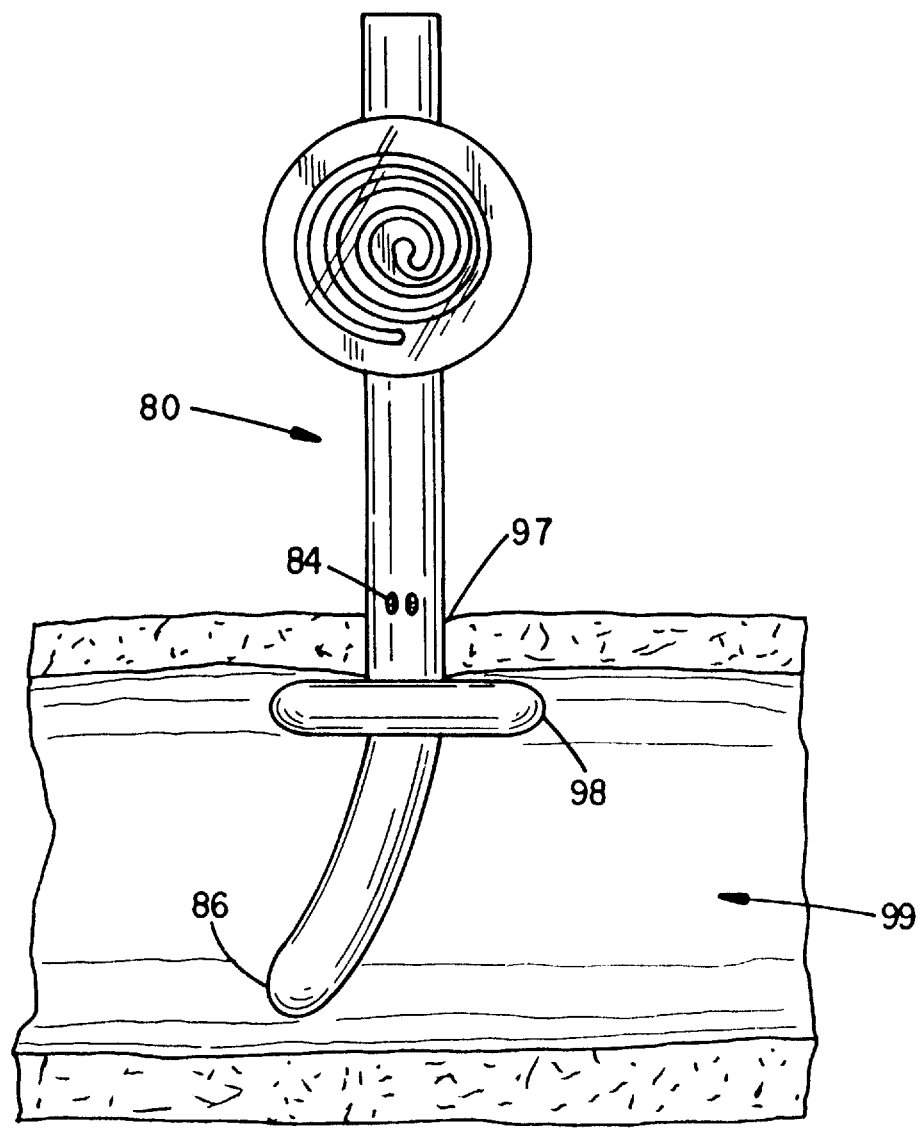
FIG. 9 is a side elevational view of first alternative embodiment of the tubular member partially removed from the blood vessel and in the second contracted position.

A first alternative embodiment of the tubular member 80 is shown in FIGS. 7–9. In this embodiment, a thin, compliant membrane forms a wall 82 between the ports 84 and the distal tip 86. A positioning wire 88 extends through the lumen and is anchored at its distal end 90 to the distal tip 86. Its proximal end 92 forms a loop or other conventional configuration for manipulation by the physician as will be explained.

The wire 88 is used to position the thin membrane wall 82 into two positions. In the first position, or relaxed position, shown in FIG. 8, the thin membrane wall 82 is substantially in line with the exterior wall surface 94 of the tubular member 80 and the distal tip exterior surface 96 resulting in a substantially smooth exterior surface. In the second position, the wire 88 is pulled in the proximal direction moving the distal tip 86 also in the proximal direction. This causes the thin membrane 82 to flex and fold forming an annular member 98 around the tubular member 80 as seen in FIG. 8.

The procedure with the first alternative embodiment is similar to that described with respect to FIGS. 4–6. The tubular member 80 is in its first position when its is introduced into the puncture site 97 and as the tubular member 80 is slowly withdrawn until the ports 84 are positioned outside the blood vessel 99 as seen in FIG. 9. When the ports 84 are positioned outside the blood vessel 99, the wire 88 is pulled in the proximal direction causing the thin membrane 82 to contract and form the annular member 98. The annular member 98 is positioned inside the blood vessel 99 adjacent to and blocking the puncture site 97 as seen in FIG. 9. The hemostatic agent is then introduced through the ports 84 and the annular member 98 prevents its entry into the blood vessel 99. After the hemostatic agent is introduced, the wire 88 is moved in the proximal direction returning the thin membrane 82 to its first position and the tubular member 80 is withdrawn before the hemostatic agent plugs the puncture site 97.

Figures 10, 11:
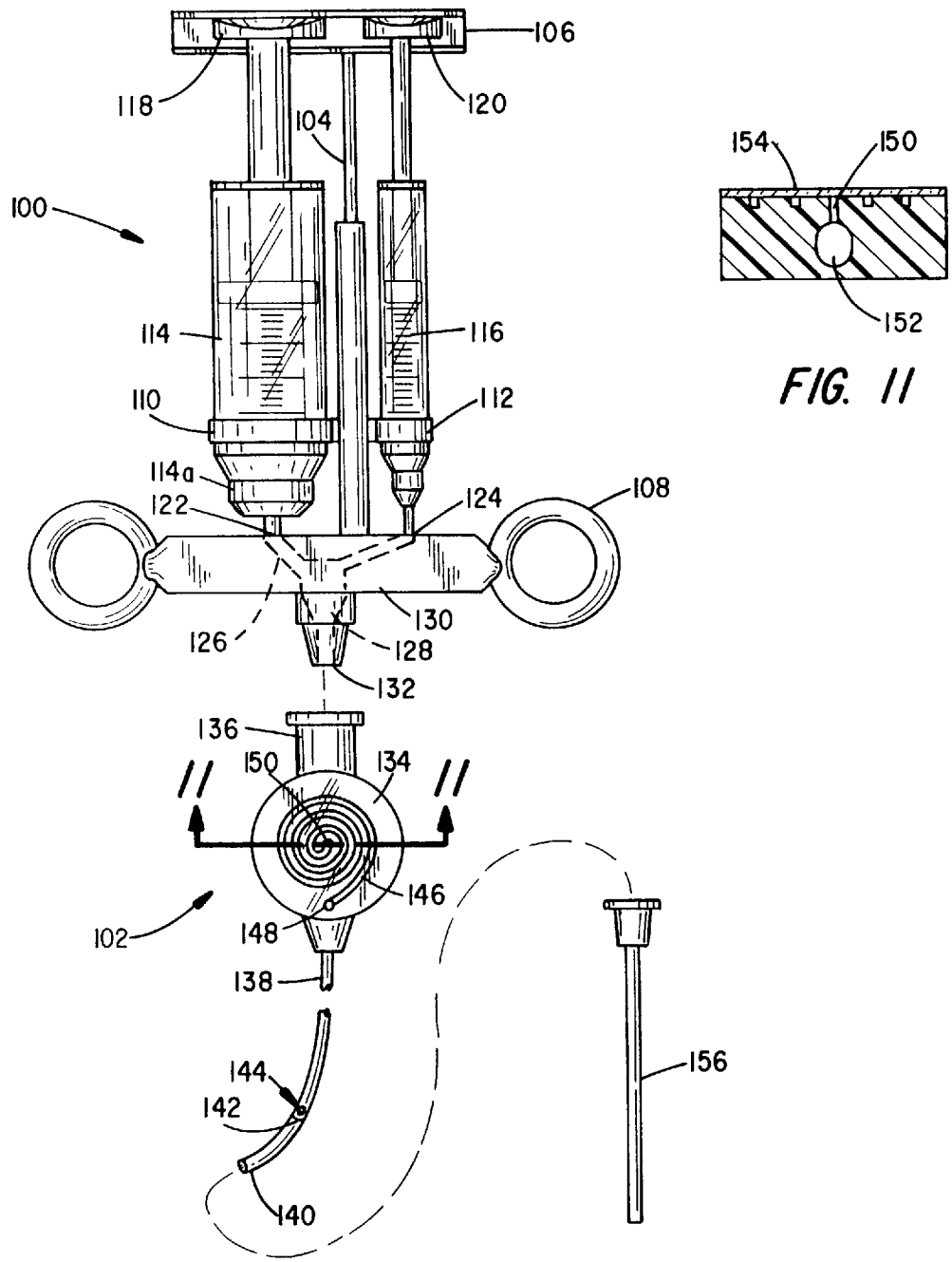
FIG. 10 is an exploded front elevational view of an syringe assembly, indicator injection tube and introducer sheath of an alternative embodiment of the present invention.
FIG. 11 is a cross-sectional view taken along line A—A in FIG. 10.

A second alternative embodiment of the indicator injection tube and introducer sheath is shown in FIGS. 10 and 11. A syringe assembly 100 is used with the indicator injection tube 102 for ejecting a platelet rich product and thrombin mixture to create hemostasis. The assembly 100 includes a plunger assembly 104 with a single plunge cap 106 at one end and finger ring assembly 108 at the other end. Syringe clips 110 and 112 help secure syringes 114 and 116 in place with the syringe plungers 118 and 120 secured in plunger cap 106. The finger ring assembly 108 operates as a manifold and includes port 122 for receiving the distal end of syringe 114 and port 124 for receiving the distal end of syringe 116. Port 122 is an inlet for passageway 126 leading to a mixing chamber 128 located within the finger ring assembly 108. Port 124 is an inlet for passageway 130 leading to the mixing chamber 128. The mixing chamber 128 then leads to an outlet port 132.

Syringe 14 is larger than syringe 116 and is intended to contain the platelet rich product. The platelet rich product is prepared by drawing blood from the patient via a hypodermic needle, and then centerfuging the blood in the syringe to cause the platelets to separate out and become concentrated at the outlet end 114A of the syringe 114. Use of the patient's own blood is desirable so there is no concern about transmitting AIDS or other blood-borne viruses to the patient. Syringe 116 contains a thrombin/activator. The size of syringes 114 and 116 are adjusted so that the desired proportions of the platelet rich product and thrombin constitute the mixed product, such as one part thrombin/activator to ten parts platelet rich product. As can be appreciated by those of skill in the art, the passageways 126 and 130 and the mixing chamber 128 are designed to create a vortex or turbulence to uniformly mix the platelet rich product and thrombin/thrombin before the mixture exits port 132.

The indicator 102 of the alternative embodiment is similar to the indicator 10 of FIGS. 1–3 and 5–6. A circular hub 134 is affixed to or integrally molded with an hemostatic seal housing 136 and an elongated tubular member 138. The elongated tubular member 138 has a soft deformable tip 140 on its distal end 142. A plurality of ports designated 144 are positioned approximate the distal end 142. A lumen (not shown) extends from the inlet housing 136 to the ports 144.

The hub 134 includes a circular enclosed track 146 which is preferably heparin coated. End 148 of the track 146 is in fluid communication with the lumen (not shown) of tube 138. End 150 of the track 146 is in fluid communication with an enlarged chamber 152 as seen in FIG. 11. The track 146 is sealed with a transparent cover 154 to form a fluid tight seal while allowing observation of a liquid moving in the track.

The indicator 102 is used with the introducer sheath 156 in the same manner described earlier with respect to the first embodiment of FIGS. 4–6. When the blood is observed to have stopped pulsating in track 146, the physician inserts outlet 132 of the syringe assembly 100 into the hemostatic seal housing 136. The physician then depresses plunger cap 106, simultaneously discharging the contents of both syringes 114 and 116. The platelet rich product from syringe 114 enters mixing chamber 128 through passageway 126 and the thrombin from syringe 116 enters mixing chamber 128 through passageway 130. The mixture then exits outlet port 132 into a lumen in the indicator 102 and then through the ports 144 into the tissue proximate the puncture in the blood vessel. The mixture creates a semi-solid plug-like material approximately two minutes after being mixed, providing sufficient time for the mixture to travel through the indicator 102 and out the ejection ports 144 before solidifying.

This invention has been described herein in considerable detail in order to comply with the patent statutes and to provide those skilled in the art with the information needed to apply the novel principals and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A device for indicating pressure variations due to systolic and diastolic phases of the cardiac cycle comprising:

(a) an elongated tubular member having a proximal end, a distal end and a lumen extending therebetween, the elongated tubular member including a port extending to the lumen proximate the distal end; and (b) an indicator device affixed to the proximal end of the tubular member, the indicator device including an elongated convoluted track formed therein, a transparent, fluid tight seal member covering said track, the track being in fluid communication with the lumen of the tubular member and adapted to receive a quantity of a liquid therein whereby the liquid reciprocally moves in said track under influence of systolic and diastolic pressure when the port is inserted through a puncture wound into a blood vessel.

2. The indicating device of claim 1 wherein the elongated convoluted track terminates in an expansion chamber of a predetermined volume.

3. The indicating device as in claim 1 wherein the distal end of the tubular member is closed and the port is a predetermined distance proximal of the closed distal end of the tubular member.

4. The indicating device as in claim 3 wherein the tubular member includes a soft, deformable elastomeric tip.

5. The indicating device as in claim 1 wherein the tubular member includes a flexible wall portion located between said port and said closed distal end whereby said flexible wall portion is movable between a first position substantially in line with outer surface of said tubular member and a second position wherein said flexible wall is positioned substantially transverse to said exterior surface of said tubular member.

6. The indicating device as in claim 5 and further including means for moving said flexible wall portion between its first position and its second position.

7. The indicating device as in claim 1 and further including an injection site on the indicator device that is in fluid communication with said lumen.

8. The indicating device as in claim 7 and further including means for injecting a hemostatic agent through the injection site.

9. The indicating device as in claim 8 wherein said means for injecting comprises a dual syringe assembly for injecting a platelet rich product and a thrombin mixture.

10. A device for indicating pressure variations due to systolic and diastolic phases of the heart comprising:

(a) a tubular member having a proximal end, a closed distal end, and a lumen extending therebetween;

(b) a port located at a predetermined distance proximal of said closed distal end of said tubular member, said port providing a fluid passageway from said lumen of said tubular member to an exterior of said tubular member;

(c) pressure indicating means including a fluid tight track of a predetermined length affixed to said proximal end of said tubular member, said fluid tight track including a transparent cover, said fluid tight track being in fluid communication with said lumen of said tubular member whereby said tubular member is adapted to be inserted into a puncture in blood vessel wall whereby blood enters the fluid tight track.

11. A device of claim 10 wherein said fluid tight track leads to an expansion chamber of a predetermined volume.

12. A device of claim 10 wherein the tubular member is of a length whereby said port will be positioned out of the distal end of the vascular introducer and said fluid tight track will be positioned out of the proximal end of said vascular introducer when said tubular member has been fully inserted into the vascular introducer.

13. A device of claim 10 wherein said tubular member includes a compliant wall portion positioned between said port and said distal end and means for moving said compliant wall portion between a first position whereby said compliant wall is substantially flush with the exterior surface of said tubular member and a second position whereby said compliant wall is substantially transverse to the exterior surface of said tubular member and thereby forming an annular member surrounding said tubular member.

14. The device as in claim 10 and further including means for injecting a hemostatic agent through the hemostatic seal into the tubular lumen whereby the hemostatic agent exits the port.

15. A device for indicating pressure variations due to systolic and diastolic phases of the heart comprising:
(a) a tubular member having a proximal end, a closed distal end, and a lumen extending therebetween, the tubular member includes a soft deformable tip made of an elastomeric material at the distal end thereof;
(b) a port located at a predetermined distance proximal of said closed distal end of said tubular member, said port providing a fluid passageway from said lumen of said tubular member to an exterior of said tubular member;
(c) pressure indicating means including a fluid tight track of a predetermined length affixed to said proximal end of said tubular member, said fluid tight track including a transparent cover, said fluid tight track being in fluid communication with said lumen of said tubular member whereby said tubular member is adapted to be inserted into a puncture in blood vessel wall whereby blood enters the fluid tight track.

16. A device for indicating pressure variations due to systolic and diastolic phases of the heart comprising:
(a) a tubular member having a proximal end, a closed distal end, and a lumen extending therebetween;
(b) a port located at a predetermined distance proximal of said closed distal end of said tubular member, said port providing a fluid passageway from said lumen of said tubular member to an exterior of said tubular member;
(c) pressure indicating means including a fluid tight track of a predetermined length affixed to said proximal end of said tubular member, said fluid tight track including a transparent cover, said fluid tight track being in fluid communication with said lumen of said tubular member wherebysaid tubular member is adapted to be inserted into a puncture in blood vessel wall whereby blood enters the fluid tight track; and
(d) a dual syringe assembly for injecting a platelet rich product and thrombin mixture.

17. An apparatus for sealing percutaneous punctures in a blood vessel wall following a catheterization procedure, said apparatus adapted for use in conjunction with a tubular introducer of the type having a sheath whose distal end is insertable into a wound resulting from percutaneous puncture of said blood vessel wall, said sealing apparatus comprising:

(a) a tubular member having a closed distal end, a proximal end and a lumen extending therebetween, said tubular member sized to slide into said tubular introducer and of a length whereby its distal end will extend out of said distal end of said tubular introducer sheath when fully inserted therein;
(b) a port positioned proximate said distal end of said tubular member, said port providing fluid passageway from said tubular member lumen to an exterior of said tubular member;
(c) a hub member affixed to said tubular member, the hub member having a groove of a predetermined length formed in a surface thereof, said groove having a first end and a second end, a first fluid passageway extending between said lumen and said first end of said groove and a transparent member over-lying the groove and cooperating with the groove to create a sealed track; and
(d) a hemostatic seal at said proximal end of said lumen.

18. The apparatus as in claim 17 and further including a compression chamber formed at said second end of said groove and in fluid communication with said sealed track, said compression chamber having a predetermined volume.

19. The apparatus as in claim 17 wherein the tubular member includes a soft deformable tip made of an elastomeric material at the distal end thereof.

20. The method of claim 19 and further including the step of completely removing said tubular member and said tubular introducer sheath from said puncture wound after injecting said hemostatic agent.

21. The apparatus as in claim 17 wherein said tubular member includes a compliant wall portion positioned between said port and said distal end and means for moving said compliant wall portion between a first position whereby said compliant wall is substantially flush with the exterior surface of said tubular member and a second position whereby said compliant wall is substantially transverse to the exterior surface of said tubular member and thereby forming an annular member surrounding said tubular member.

22. The apparatus as in claim 17 and further including means for injecting a hemostatic agent through the hemostatic seal into said lumen.

23. The apparatus as in claim 17 wherein means for injecting comprises a dual syringe assembly for injecting a platelet rich product and thrombin mixture.

24. A method of sealing percutaneous punctures in the blood vessel of a patient following a catheterization procedure and adapted for use with a vascular introducer of the type having a sheath whose distal end is inserted into a wound resulting from the percutaneous puncture, said method comprising the steps of:
(a) providing a tubular member having a closed distal end, a proximal end and a lumen extending therebetween, said tubular member having a port located a predetermined distance proximal of its closed distal end, said port extending between said lumen and an exterior of said tubular member and an observable blood receiving fluid tight track positioned proximate said proximal end of said tubular member, said fluid tight track being in fluid communication with said lumen;
(b) inserting said tubular member into said tubular introducer sheath until blood movement is observed in said fluid tight track;
(c) retracting as a unit from said puncture wound said tubular member and said tubular introducer sheath until blood movement in said fluid tight track ceases; and (d) injecting a hemostatic agent into said tubular member lumen whereby said hemostatic agent exits said port adjacent said blood vessel wall.

25. The method of claim 24 and further including the step of forming an annular member to surround said tubular member at a location on an interior of said blood vessel adjacent said puncture prior to injecting said hemostatic agent.

26. The method of claim 25 and further including the step of removing the annular member surrounding said tubular member prior to removing said tubular member.

27. The method of claim 24 and further including the step of selecting the hemostatic agent from the class consisting of thrombin, fibrin, fibrin glue, methacrylates, cyanoacrylates, collagen, platelet agonists and vasoconstrictor drugs.

28. The method of claim 27 and further including the step of selecting the vasoconstrictor drugs from the group consisting of phenylephrine, norepinephrine, epinephrine, prostaglandin F2 alpha, endothelin, methergine, oxytocin and isoprel.

29. The method of claim 24 and further including the steps of obtaining the hemostatic agent by obtaining a platelet rich product from the patient and mixing said platelet rich product with a thrombin.

\* \* \* \* \*